US00PP31345P2

(12) United States Plant Patent
Pierron-Darbonne

(10) Patent No.: US PP31,345 P2
(45) Date of Patent: Jan. 14, 2020

(54) BLUEBERRY PLANT NAMED 'PLABLUE 1545'

(50) Latin Name: ***Vaccinium corymbosum* L.**
Varietal Denomination: Plablue 1545

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal (ES)

( * ) Notice: Subject to any disclaimer, the term of this patent is extended or adjusted under 35 U.S.C. 154(b) by 0 days.

(21) Appl. No.: 16/501,257

(22) Filed: Mar. 13, 2019

(30) Foreign Application Priority Data

Aug. 9, 2018 (QZ) ..... PBR 2018/2073

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
*Assistant Examiner* — Karen M Redden
(74) *Attorney, Agent, or Firm* — Knobbe, Martens, Olson & Bear, LLP

(57) ABSTRACT

Described is a new and distinct blueberry variety with varietal denomination 'Plablue 1545', characterized by a combination of traits which include, weak vigor plant, semi upright plant growth habit, and very abundant production of large fruit-size, oblate shaped and very firm fruit. 'Plablue 1545' is a self-fertile variety.

16 Drawing Sheets

Botanical classification: *Vaccinium corymbosum* L.

Variety denomination: The new plant has the varietal denomination 'Plablue 1545'.

CROSS-REFERENCE TO RELATED APPLICATIONS

This application claims the benefit of European Community Plant Variety Office Application No. 2018/2073, for a blueberry variety named 'Plablue 1545,' filed on Aug. 9, 2018, the entirety of which is incorporated by reference herein.

BACKGROUND

Disclosed herein is a new and distinct southern highbush blueberry variety (*Vaccinium corymbosum* L.). The varietal denomination of the new variety is 'Plablue 1545.' The new variety of blueberry was created in a breeding program by crossing two parents; in particular, by crossing as seed parent an undistributed blueberry parent designated 14.027.001 (unpatented) and as pollen parent an undistributed blueberry parent designated 14.049.001 (unpatented). Female and male are selections from breeder's program of the applicant. Both parental varieties are property of the applicant and have not been commercialized.

The new variety was grown and asexually propagated by softwood cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between about November 20 and June 22 of the following year.

SUMMARY

The present invention relates to a new and distinct southern highbush blueberry variety. The varietal denomination of the new variety is 'Plablue 1545', that produces and maintains a weak vigorous plant with consistent fruit production from beginning January through middle June. Among the characteristics which appear to distinguish the new variety from other varieties are a combination of traits which include a weak vigor plant, semi upright plant growth habit, and very abundant production of large fruit-size, oblate shaped and very firm fruit.

The new blueberry plant variety 'Plablue 1545' has not been observed under all possible environmental conditions. The phenotype may vary somewhat with variations in environmental and cultural practices such as temperature and light intensity without, however, any variance in genotype.

COMPARISON TO THE PARENTS

The new variety is distinguished from its parents by the following characteristics which are different than the seed parent designated '14.027.001' (unpatented) and the pollen parent designated '14.049.001' (unpatented).

Size of corolla tube in the flower of seed parent '14.027.001' (unpatented) is higher than in the flower of 'Plablue 1545'.

Seed parent '14.027.001' (unpatented) shows a rounded fruit shape, whereas 'Plablue 1545 shows an oblated fruit shape.

Depth of the calyx basin of fruit of seed parent '14.027.001' (unpatented) is deep, whereas the depth of the calyx basin of fruit of 'Plablue 1545' is medium.

Leaf of pollen parent '14.049.001' (unpatented) shows an elliptic shape, whereas leaf of 'Plablue 1545' shows a lanceolate shape.

Pollen parent '14.049.001' (unpatented) shows a short length of internode on one-year-old shoot, whereas 'Plablue 1545' shows a medium length.

Fruit of pollen parent '14.049.001' (unpatented) shows a shallow depth of the calyx basin, whereas fruit of 'Plablue 1545' shows a medium depth of the calyx basin.

COMPARISON TO CLOSEST VARIETY

The new variety is closest to the variety 'Biloxi' (unpatented), but is distinguished therefrom by the following characteristics which are different than 'Biloxi'.

Ratio of length/width of the leaf of 'Biloxi' (unpatented) is longer than the ratio of length/width of the leaf of 'Plablue 1545'.

Shape of the leaf of 'Biloxi' (unpatented) is elliptic, whereas shape of the leaf of 'Plablue 1545' is lanceolate.

Length of inflorescence of 'Biloxi' (unpatented) is shorter than the length of inflorescence of 'Plablue 1545'.

Density of fruit cluster of 'Biloxi' (unpatented) is higher than the density of fruit cluster of 'Plablue 1545'.

'Biloxi' (unpatented) shows a smaller fruit size and less firm fruit than the fruit of 'Plablue 1545'.

Depth of the calyx basin in the fruit of 'Biloxi' (unpatented) is shallow, whereas depth of the calyx in the fruit of 'Plablue 1545' is medium.

Fruiting type of plant of 'Biloxi' (unpatented) is on one-year-old and current season's shoots, whereas fruiting type of plant of 'Plablue 1545' is on one-year-old shoots only.

Time of beginning of flowering on one-year-old shoot of 'Biloxi' (unpatented) is less early than in 'Plablue 1545'

Time of beginning of fruit ripening on one-year-old shoot of 'Biloxi' (unpatented) is less early than in 'Plablue 1545'.

Differences in the ratio of length/width and the shape of the leaf of 'Plablue 1545' (designated 15.09.020) and 'Biloxi' (unpatented) are shown in FIG. 3 and FIG. 13. Differences in density of fruit cluster of 'Plablue 1545' (designated 15.09.020) and 'Biloxi' (unpatented) are shown in FIG. 8 and FIG. 14. Differences in fruit size of 'Plablue 1545' (designated 15.09.020) and 'Biloxi' (unpatented) are shown in FIG. 9 and FIG. 15. Differences in depth of calyx basin in the fruit of 'Plablue 1545' (designated 15.09.020) and fruit of 'Biloxi' (unpatented) are shown in FIG. 11 and FIG. 16. These differences are maintained during the harvest season.

BRIEF DESCRIPTION OF THE ILLUSTRATIONS

The accompanying photographs show typical specimens of the new variety, designated 15.09.020 in the illustrations, including fruit, foliage and flower, in color as nearly true as it is reasonably possible to make in color illustrations of this character.

The plants depicted in the drawings were planted October 14 in the farm of La Mogalla in Cartaya (Huelva), Spain, about 7° W, 37° N, 45 feet elevation.

Drawings/photographs were taken April (about April 4 and April 12): minimum temperate about 7° to 9° Centigrade, maximum temperate about 18 to 22° Centigrade.

FIG. 1 and FIG. 2 show several plants of the new variety (designated 15.09.020) which exhibit a semi upright habit plant with several clusters of violet-blue color fruit RHS Violet-Blue group color near 97 C to 97 B) with wax and oblated shape fruits.

FIG. 3 and FIG. 4 show the upper side and the underside, respectively, of a complete leave of the new variety (designated 15.09.020). In it, we can see that the leaf color of upper side of the new variety (designated 15.09.020) is a yellow-green color (RHS Yellow-Green group near 148 B to 148 A) and the leaf color of underside of the new variety (designated 15.09.020) is a yellow-green color (RHS Yellow-Green group color near 146 C to 146 B). We can see the lanceolate shape of leaf of the new variety (designated 15.09.020).

FIG. 5 shows an immature flower of the new variety (designated 15.09.020). In it, we can see the immature flower red color (RHS Red group color near 39 D to 39 C).

FIG. 6 shows a typical flower of the new variety (designated 15.09.020). In it, we can see the corolla of the new variety (designated 15.09.020) with white color (RHS White group color near 155 B to 155 A).

DESCRIPTION OF THE NEW VARIETY

Figure 1:
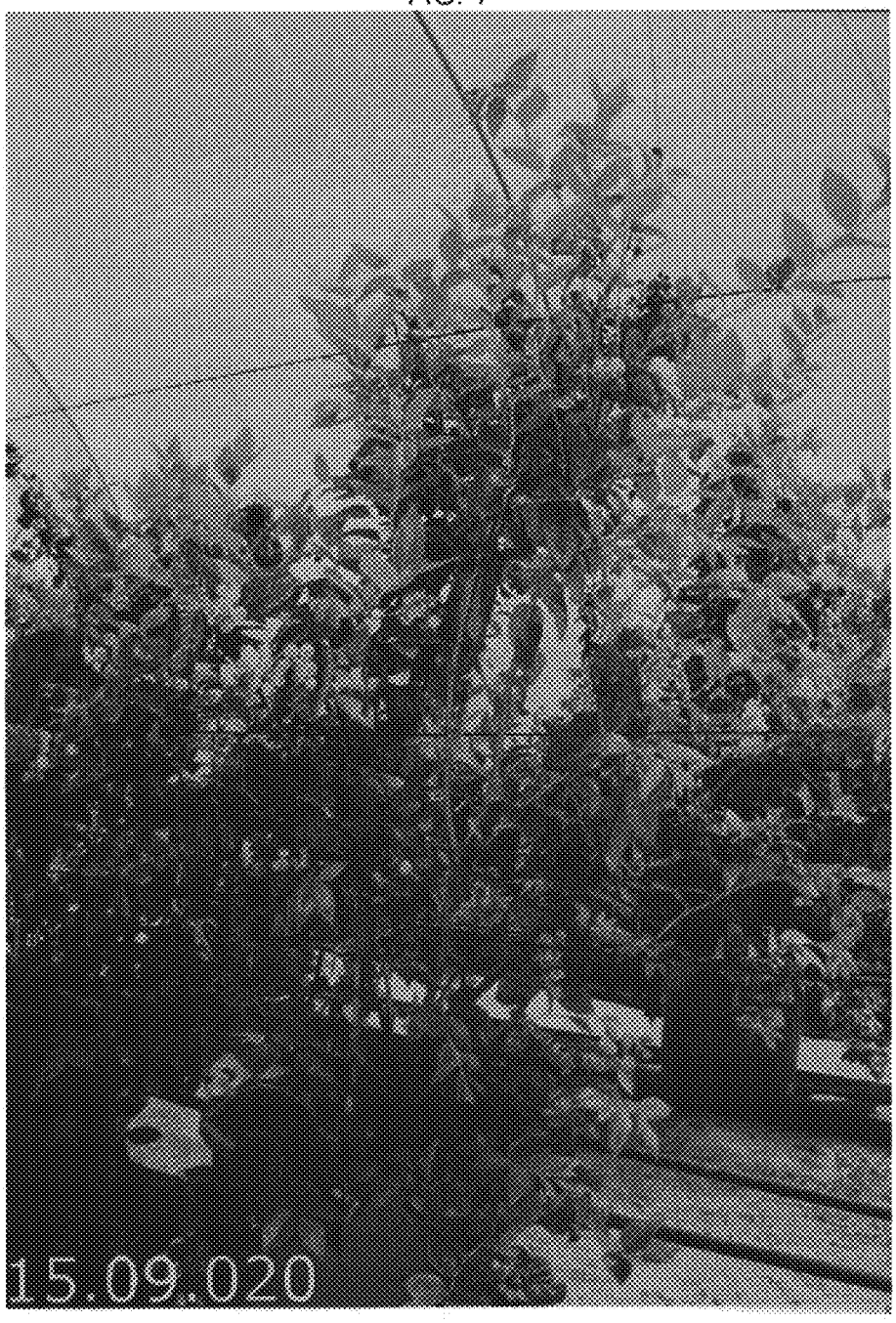
Figure 2:
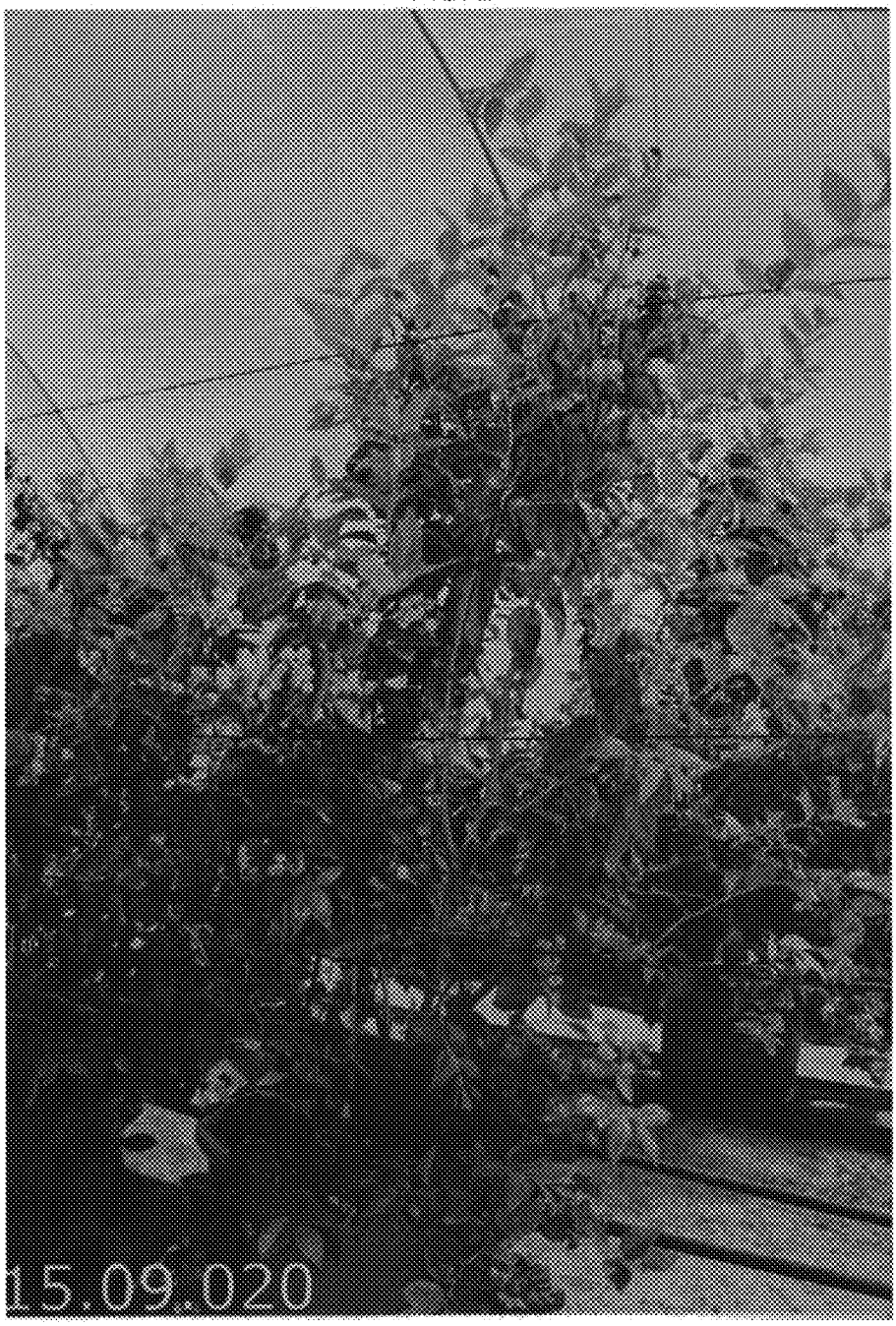
Figure 3:
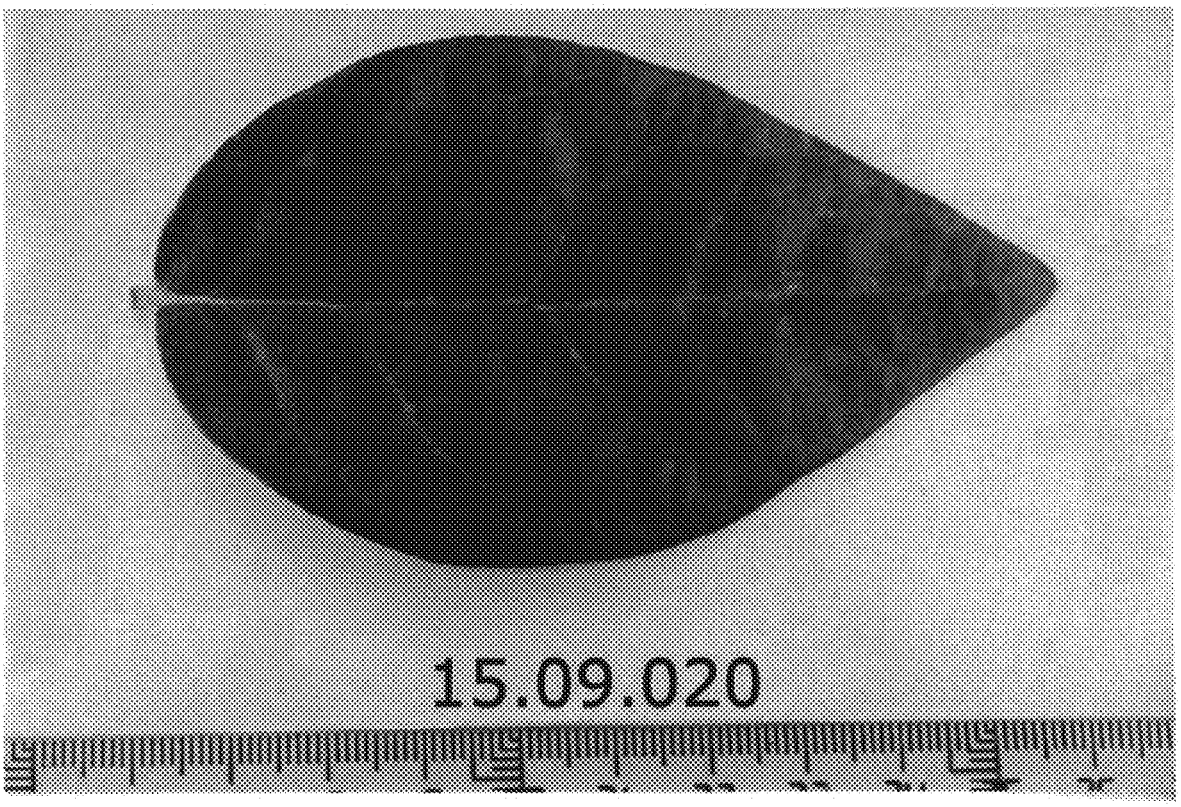
Figure 4:
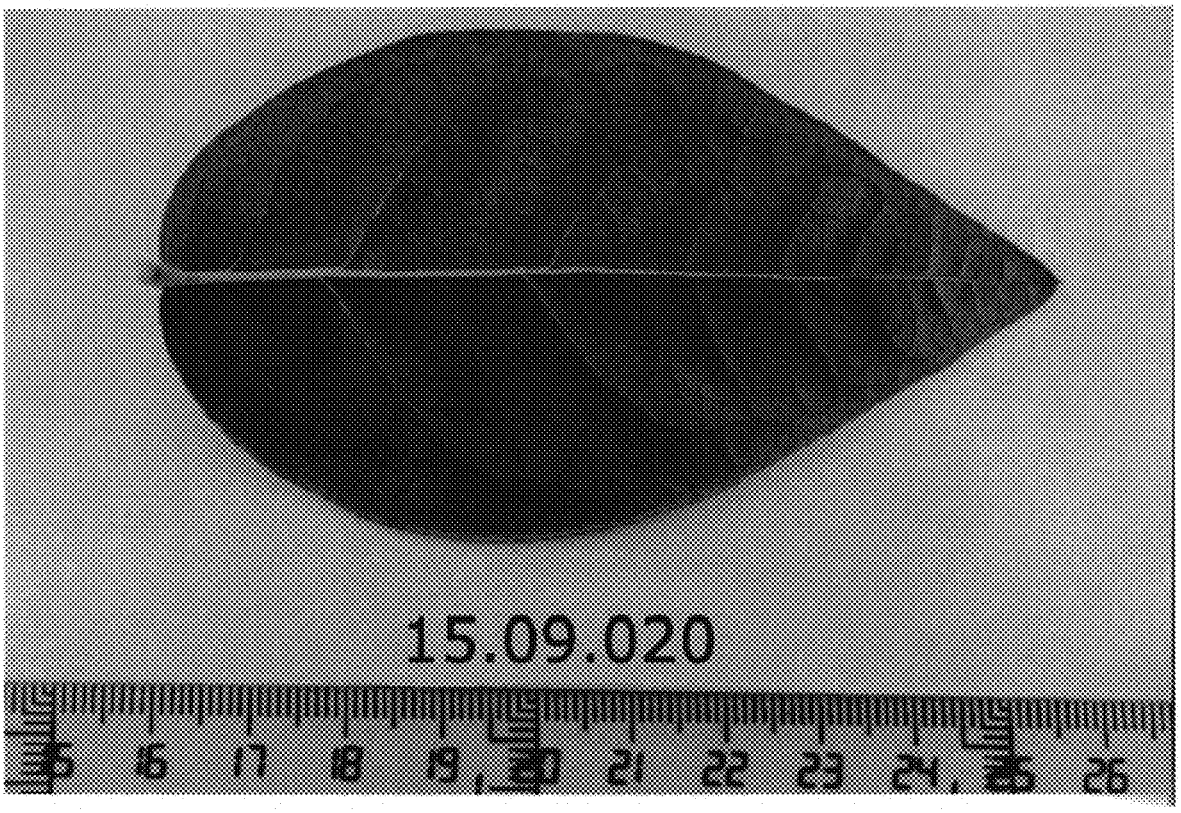
Figure 5:
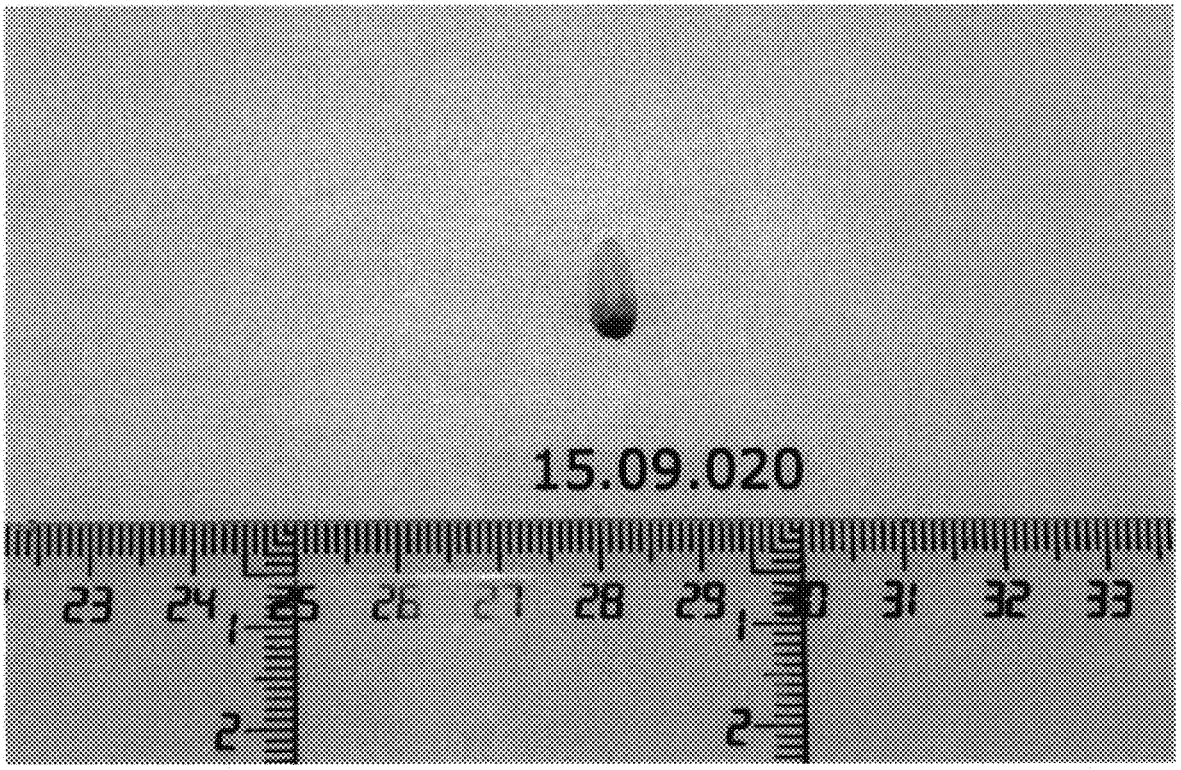
Figure 6:
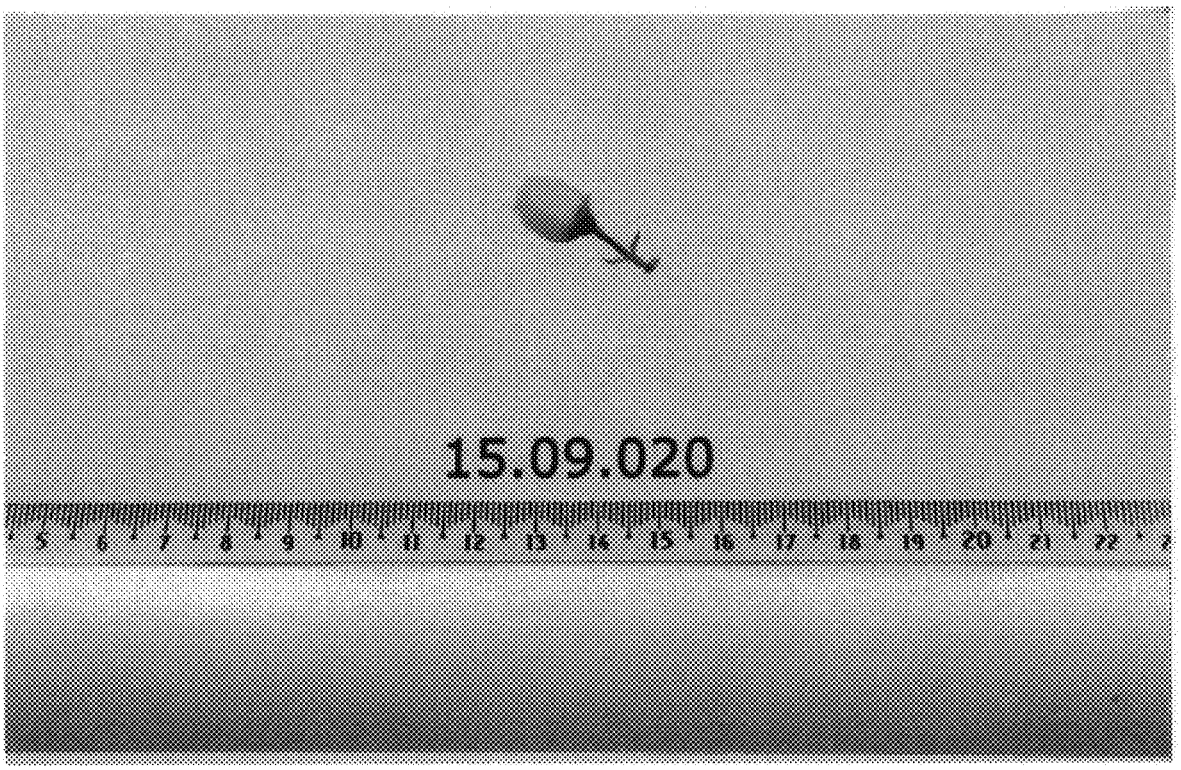
Figure 7:
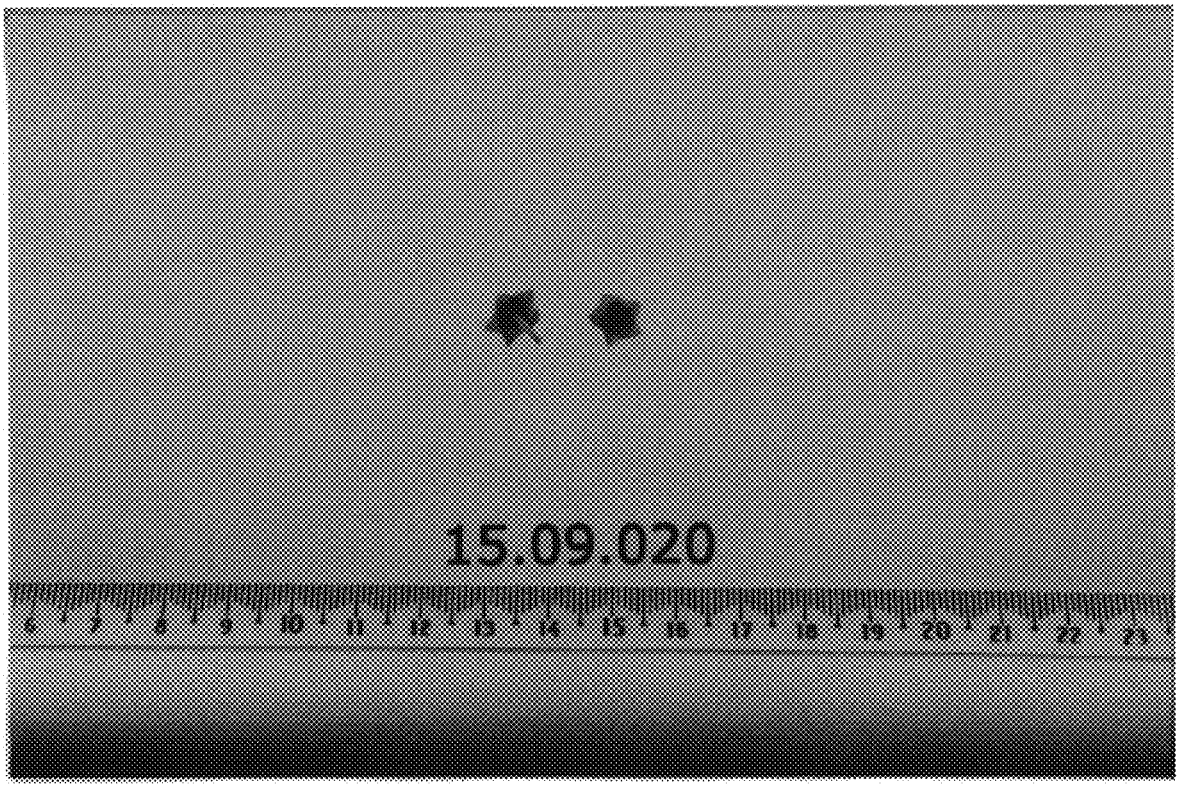
FIG. 7 shows typical sepals of the new variety (designated 15.09.020) with yellow-green color (RHS Yellow-Green group color near 145 C to 145 B).
Figure 8:
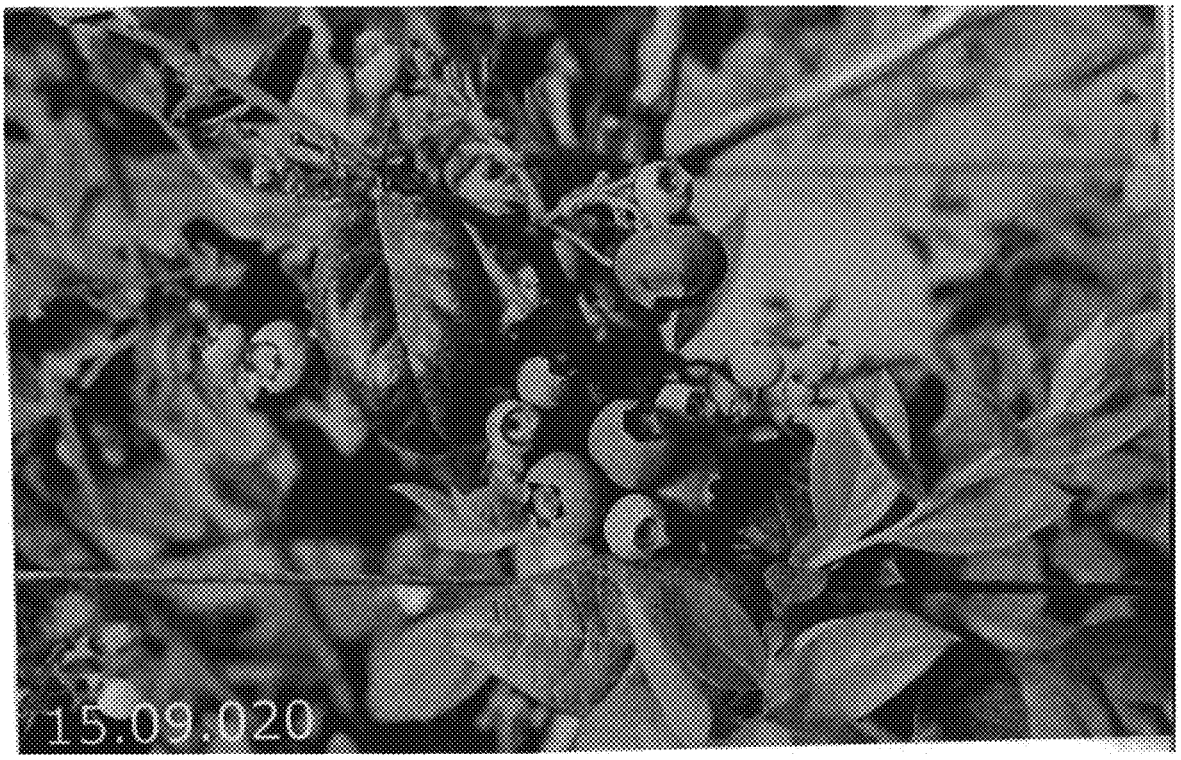
FIG. 8 shows the density of fruit cluster of the new variety (designated 15.09.020).
Figure 9:
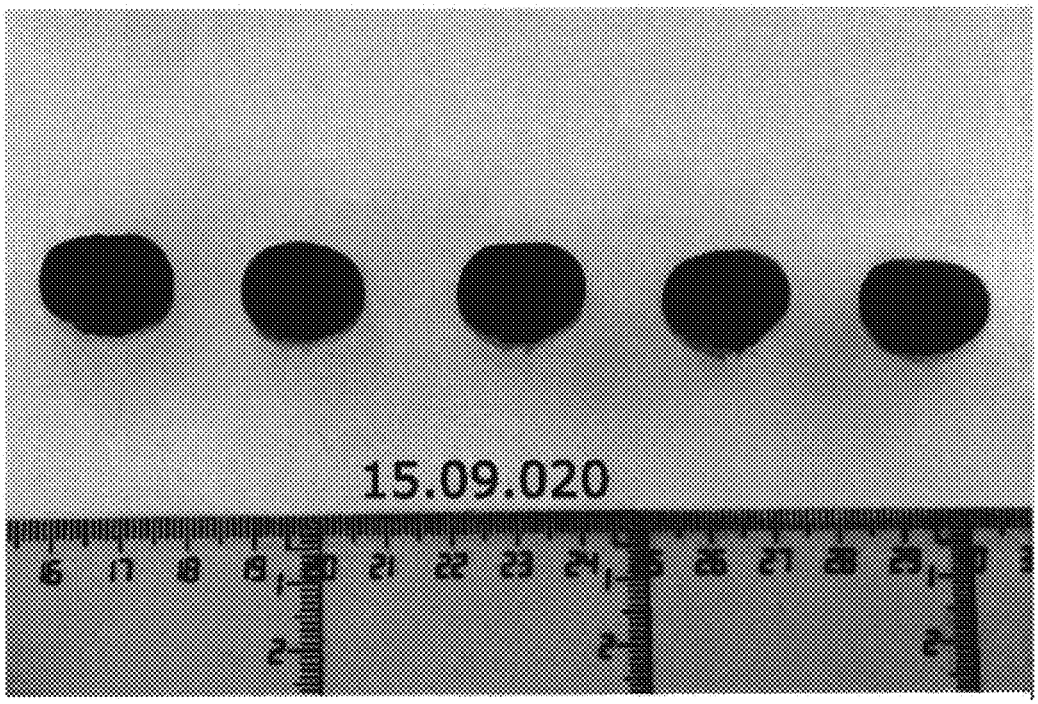
FIG. 9 and FIG. 10 show typical fruits of the new variety (designated 15.09.020) with oblate shape and violet-blue color with wax (RHS Violet-Blue group color near 97 C to 97 B).
Figure 10:
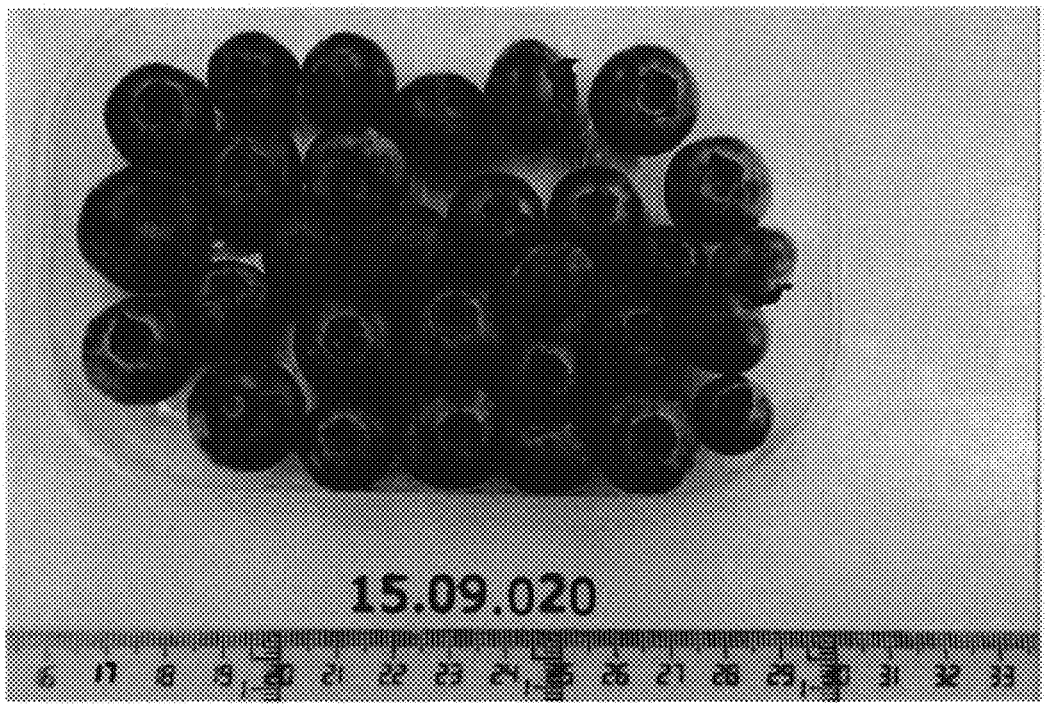
Figure 11:
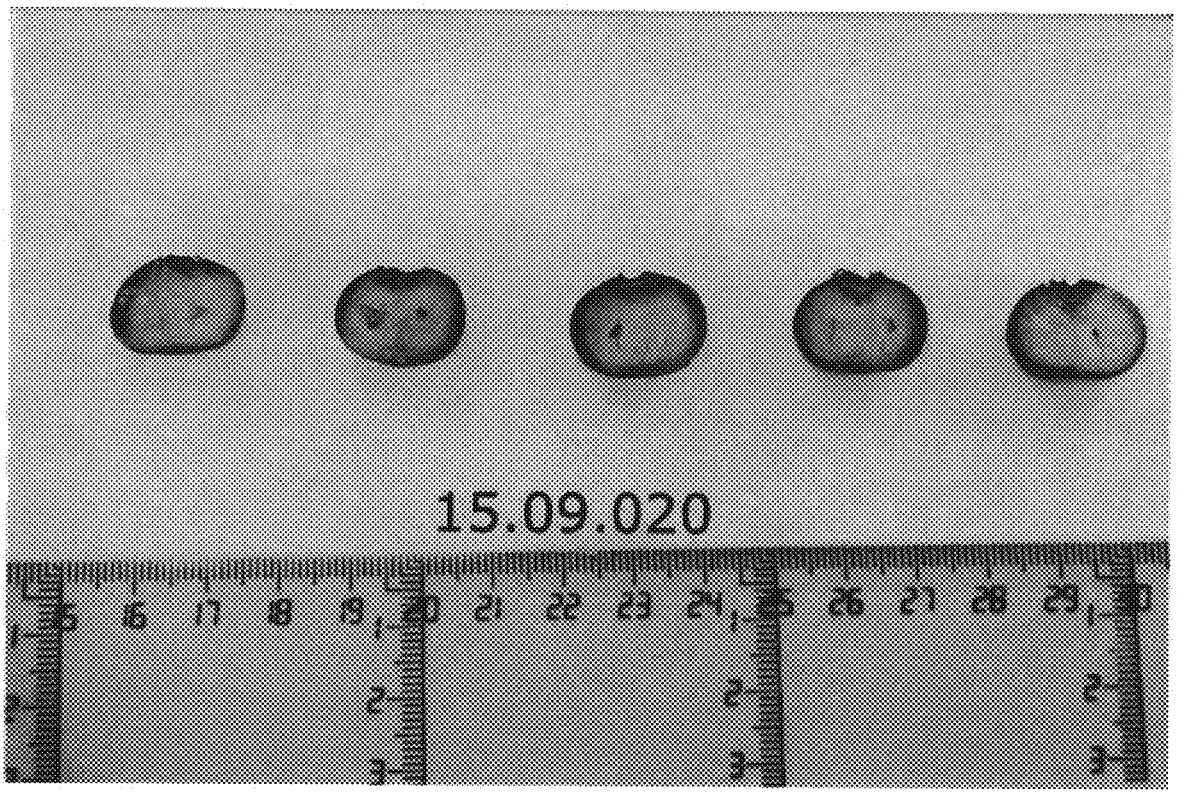
FIG. 11 shows typical sliced fruits of the new variety (designated 15.09.020) with yellow-green flesh color (RHS Yellow-Green group color near 151 D to 151 B).
Figure 12:
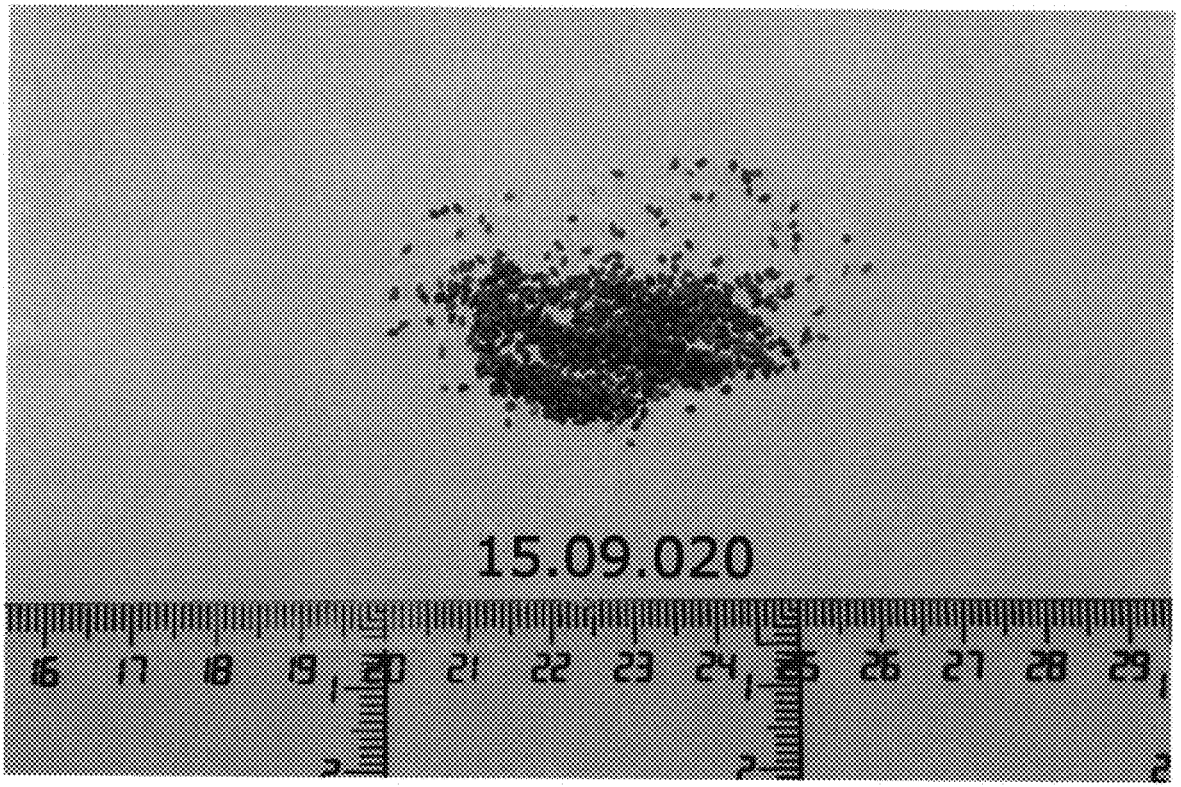
FIG. 12 shows typical seeds of the new variety (designated 15.09.020) with greyed-orange color RHS Greyed-Orange group color near 164 B to 164 A.
Figure 13:
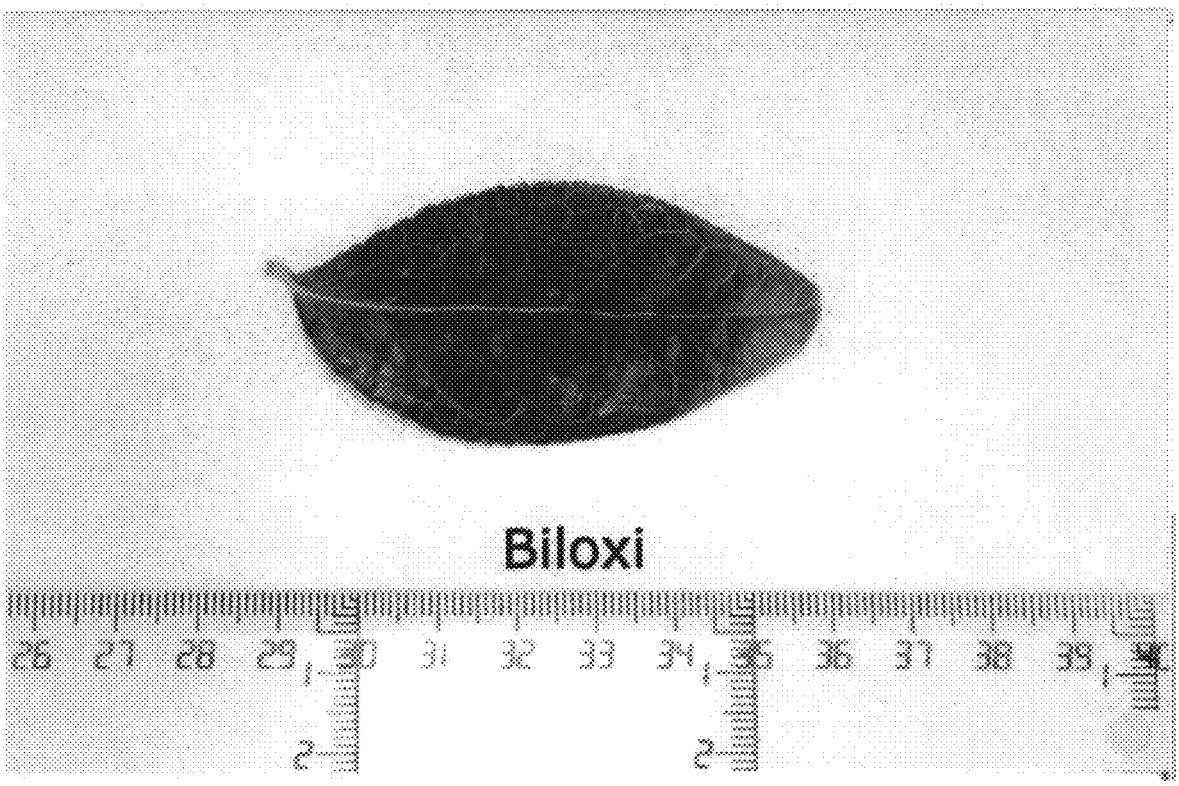
FIG. 13 shows the leaf of blueberry variety 'Biloxi' (unpatented), which exhibits an elliptic shape.
Figure 14:
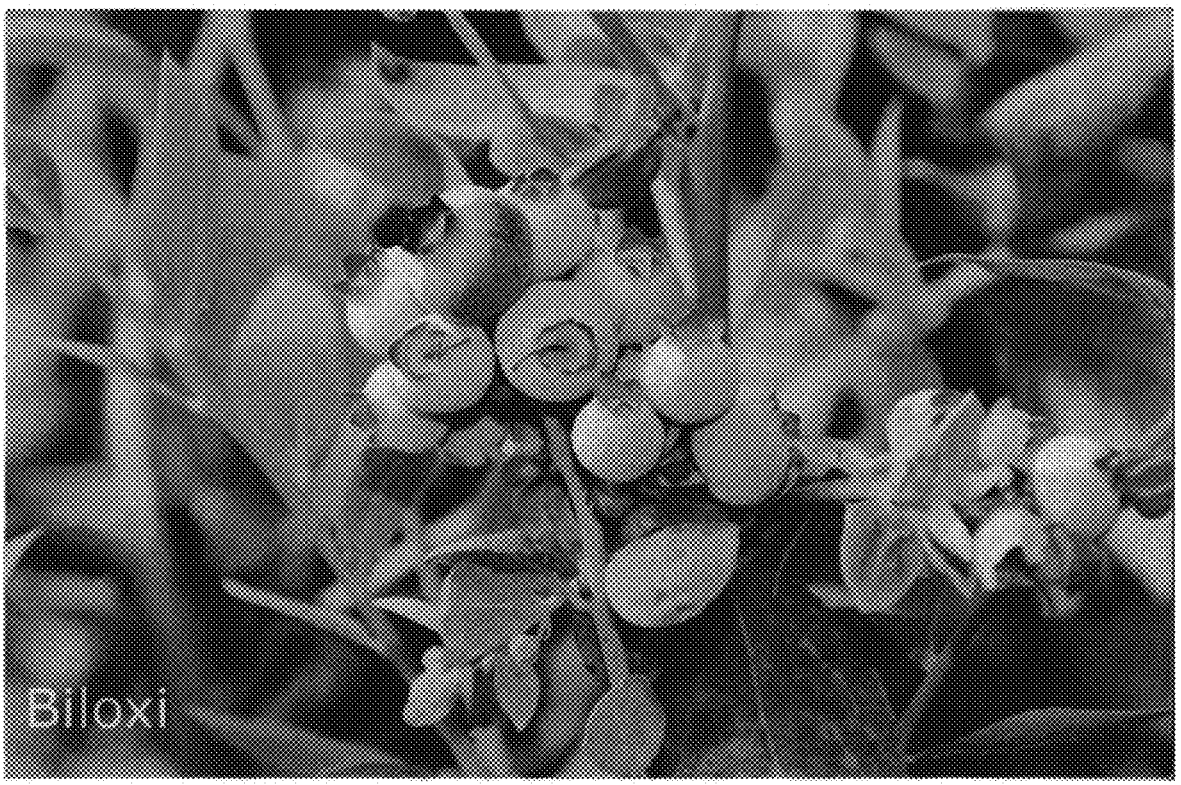
FIG. 14 shows the density of fruit cluster of 'Biloxi' (unpatented).
Figure 15:
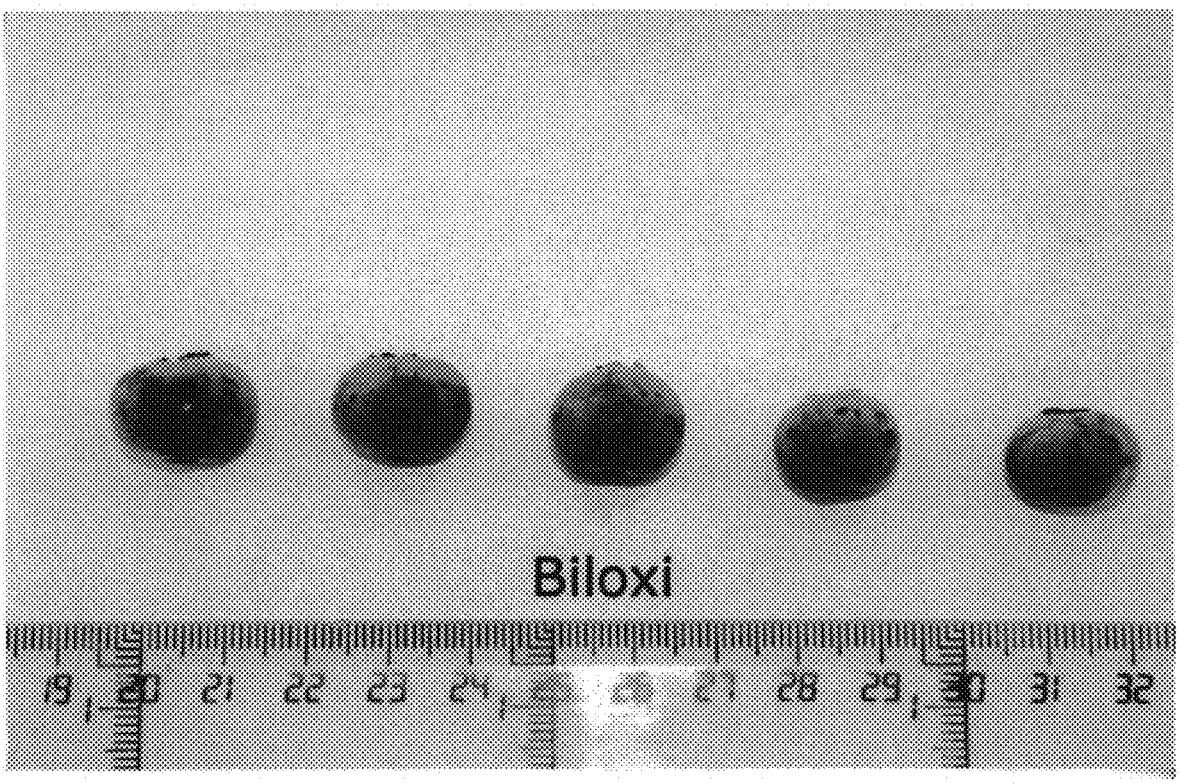
FIG. 15 shows the fruit of blueberry variety 'Biloxi' (unpatented), which exhibits a fruit size smaller than the fruit of the new variety (designated 15.09.020).
Figure 16:
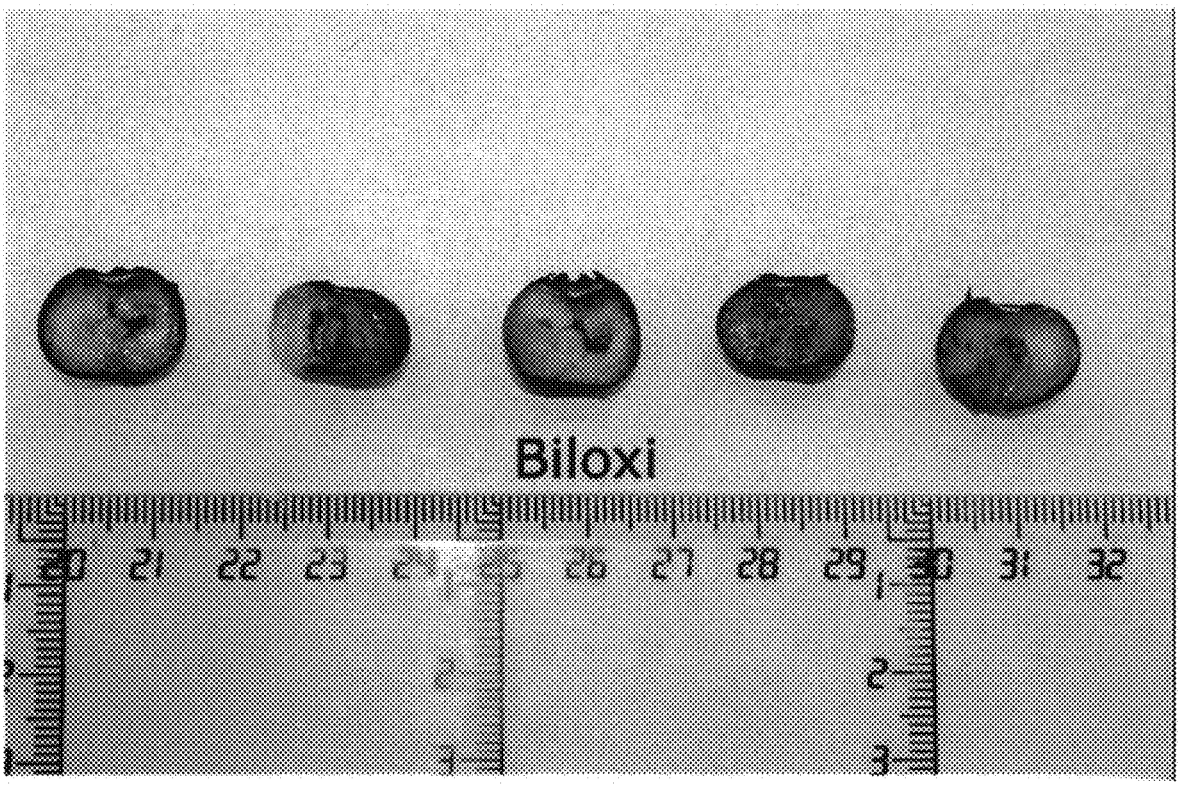
FIG. 16 shows several fruits of blueberry variety 'Biloxi' (unpatented), which exhibit a shallow depth of the calyx basin.

The following detailed description of the new variety is based upon observations taken of plants and fruits grown "underglass", i.e. undertunnel, in the farm of La Mogalla in Cartaya (Huelva), Spain, 7° W., 37° N., 45 feet elevation.

The following description is in accordance with UPOV terminology and the color teminology herein is in accordance with The Royal Horticultural Society Colour Chart (R.H.S.C.C.), 3$^{rd}$ edition published in 1995. The color descriptions and other phenotypical descriptions may deviate from the stated values and descriptions depending upon variation in environmental, seasonal, climatic and cultural conditions.

PROPAGATION

The new variety is principally propagated by softwood cuttings. Although propagation by softwood cuttings is presently preferred, other know methods of propagating blueberry plants may be used.

Blueberry root and develop well after transplanting.

GENERAL

'Plablue 1545' is propagated by softwood cuttings. It is a variety with fruit production from beginning January through middle June. It is a self-fertile variety. It produces large quantities of pollen throughout the seasons and pollination is good.

Production: Plants described are from high elevation nursery in Segovia, Spain, 3° 59'W., 41° 22'N., 2742 feet elevation.

Trials pursued in Cartaya (Huelva), Spain.

Date of planting: 14th October

Number of repetitions: 2

Plants per repetition: 50

TABLE 1

Table 1 shows the accumulated production of fruit (g/plant) of the new variety 'Plablue 1545' when compared to its closest varieties 'Biloxi' and 'Star' (U.S. Plant Pat. No. 10,675).

| Variety | February 27 | March 31 | April 30 | June 22 |
|---|---|---|---|---|
| Plablue 1542 | 1194.00 | 1731.00 | 2453.00 | 4047.67 |
| Biloxi | 191.67 | 477.33 | 905.33 | 2850.00 |
| Star | 0.00 | 757.67 | 1781.73. | 1803.10 |

TABLE 2

Table 2 shows the weight (g/fruit) at three dates of the new variety 'Plablue 1545' when compared to its closest varieties 'Biloxi' and 'Star'.

| Variety | March 31 | April 30 | June 22 |
|---|---|---|---|
| Plablue 1542 | 19.00 | 19.00 | 17.00 |
| Biloxi | 16.00 | 14.00 | 14.00 |
| Star | 18.00 | 18.00 | 17.00 |

**Weight is shown as the average weight per fruit

DETAILED DESCRIPTION OF THE NEW VARIETY

The following additional information is provided to further describe the new variety.

Variety: 'Plablue 1545'. Breeder Ref. 15.09.020.

Latin name: *Vaccinium corymbosum* L.

Common name: Southern highbush blueberry.

Plants are growing in containers of 45 liters of capacity.

Plant:

*Habit*.—Semi upright.

*Vigor*.—Weak.

*Height of plant*.—About 1.50 to 1.60 m.

*Canopy diameter*.—About 1.75 to 1.85 m.

*Twigginess*.—Medium.

*Suckering*.—Low.

*Evergreenness*.—Evergreen.

*Chilling requirement*.—Approximately 100-200 hour at temperatures at or below 7° C.

*Cold hardiness*.—Has not been grown in all environments including harsh winter environments. Cold tolerance is expected to be low.

Trunk and branches:

*Surface texture new wood*.—Smooth.

*Surface texture* 1 *year wood*.—Smooth.

*Surface texture* 2 *years and older wood*.—Rough.

*Diameter new wood*.—About 5.0 to 6.0 mm.

*Diameter* 1 *year wood*.—About 9.0 to 10 mm.

*Diameter* 2 *years old wood*.—About 18.0 to 19.0 mm.

*Color*.—New wood about yellow-green color (RHS Yellow-Green group color near 144C to 144 B) transitioning to about greyed-orange color (RHS Greyed-Orange group color near 177 C to 177 B) in about 2 year old wood.

Leaf:

*Internode length*.—About 22.0 to 24.0 mm.

*Leaf arrangement*.—Alternate simple.

*Length*.—About 9.0 to 9.5 cm.

*Width*.—About 5.0 to 5.5 cm.

*Leaf shape*.—Lanceolate.

*Shape of tip*.—Acute.

*Shape of base*.—Obtuse.

*Shape of margin*.—Entire.

*Venation pattern*.—Reticulate.

*Mature leaf color upperside*.—RHS Yellow-Green group color near 148 B to 148 A.

*Mature leaf color underside*.—RHS Yellow-Green group color near 146 C to 146 B.

*Pubescence upper leaf surface*.—Absent.

*Pubescence under leaf surface*.—Absent.

*Pubescence leaf margin*.—Absent.

*Precocity*.—New vegetative growth before flowering.

Petiole:

*Length*.—About 2.5 to 3.0 mm.

*Width* (*diameter*).—About 3.0 to 3.20 mm.

*Texture*.—Smooth.

*Color*.—RHS Yellow-Green group color near 145 C to 145 B.

Flower:

*Flower arrangement*.—Compound raceme. Clusters at the end of branches.

*Flower shape*.—Urceolate.

*Flowers per cluster*.—About 7 to 9.

*Flower fragrance*.—Pleasant. Sweet.

*Immature flower color*.—RHS Red group color near 39 D to 39 C.

Corolla:

*Length*.—About 7.0 to 7.5 mm.

*Diameter*.—About 6.0 to 7.0 mm.

*Aperture width*.—About 3.0 to 4.0 mm.

*Color*.—RHS White group color near 155 B to 155 A.

*Texture*.—Smooth.

Peduncle:

*Length*.—About 14.5 to 15.0 mm.

*Color*.—RHS Yellow-Green group color near 144 C to 144 B.

Pedicel:

*Length*.—About 12.5 to 13.0 mm.

*Color*.—RHS Yellow-Green group color near 144 C to 144 B.

*Calyx (with sepals) diameter.*—7.5 to 8.5 mm.
*Calyx texture.*—Smooth.
*Color center of calyx.*—RHS Green group color near 143 C to 143 B.
*Color sepals.*—White color (RHS White group color near 155 B to 155 A).
*Attitude of sepals.*—Erect.
*Type of sepals.*—Reflexed.

Stamen:
*Length.*—About 4.5 to 5.0 mm.
*Number per flower.*—About 14 to 15.
*Filament color.*—RHS Yellow-Green group color near 145 C to 145 B.

Style:
*Length.*—About 7.0 to 7.5 mm.
*Color.*—RHS Green group color near 145 C to 145 B.

Pistil:
*Length.*—About 8.5 to 8.9 mm.
*Ovary color.*—RHS Yellow-Green group color near 145 D to 145 C.

Anther:
*Length.*—About 3.4 to 3.7 mm.
*Number.*—About 14 to 15.
*Color.*—RHS Greyed-Orange group color near 165 B to 165 A.

Pollen:
*Abundance.*—Medium.
*Color.*—RHS Yellow-Orange group color near 20 C to 20 B.
*Self-compatibility.*—The cultivar has demonstrated a medium high degree of self-compatibility.

Fruit:
*Fruiting type.*—On one-year-old only.
*Calyx aperture.*—About 7.0 to 8.0 mm.
*Calyx lobes.*—About 5 to 6 lobes.
*Calyx depth.*—About 2.3 to 2.5 mm.
*Pedicel length.*—About 11.0 to 12.0 mm.
*Pedicel surface texture.*—Smooth.
*Peduncle length.*—About 12.5 to 13.0 mm.
*Peduncle surface texture.*—Smooth.
*Berries per cluster.*—About 5 to 9.
*Berry detachment.*—Easy.
*Weight.*—About 17 to 19 grs.
*Height.*—About 13.0 to 14.0 mm.
*Width.*—About 18.0 to 19.0 mm.
*Shape.*—Oblate.
*Color with wax.*—RHS Violet-Blue group color near 97 C to 97 B.
*Color with wax removed.*—RHS black group color near 202 A.
*Wax.*—Moderately persistent.
*Surface wax abundance.*—Moderate.
*Flesh color.*—RHS Yellow-Green group color near 151 D to 151 B.
*Pedicel scar.*—About 1.0 to 1.7 mm.
*Firmness.*—0.9 Kg. Firmness: It is the fruit's resistance to penetration measured in Kilograms (Kg). The measure given has been obtained by the penetrometer ROZE Mod. Arbelette, with a 20 mm2 section head.
*Texture of flesh.*—Crisp.

Seed:
*Color.*—RHS Greyed-Orange group color near 164 B to 164 A.
*Length.*—About 1.0 to 2.0 mm.
*Width.*—About 0.90 to 1.0 mm.
*Weight.*—About 0.3 to 0.4 mg.
*Seeds per berry.*—About 14 to 16.

General: The growing period in Huelva, Spain, where the observations on primocane production were made, is between about November 20 and June 22 of the following year. 'Plablue 1545' is a blueberry variety that benefits from induction to flowering by chilling, usually a few hours (approximately 100-200 hours) are sufficient, preferably at temperatures of 7° C. or less. Normally, the minimum number of hours is accumulated in the field during several days. 'Plablue 1545' is a variety with consistent fruit production beginning in on first days of January and ending at the middle of June. After planting as aforesaid, plants are grown in containers under tunnel. Water and fertilizer were applied through drip irrigation.

Date of planting: About October 15 in the farm of La Mogalla, in Cartaya (Huelva), Spain, about 7° W, 37° N, 45 feet elevation. Time of flowering data: 10% flowering about September 24. First mature fruits are about January 4 (15-20 g/plant), with a maximum production at the middle of May.

Storage qualities: 'Plablue 1545' fruit maintains their quality characteristics when keeping them in a frigo chamber at temperatures of about 2° C. for a duration of about 24 days. The fruit's color remains substantially the same. Shelf life of 'Plablue 1545' is good.

Use/market: The berries of 'Plablue 1545' are suitable for consumption as fresh fruit. Also, they are amenable to processing.

Disease resistance: No particular sensitivity to any disease or pest has been observed for 'Plablue 1545'

I claim:

1. A new and distinct blueberry plant of the variety substantially as shown and described.

* * * * *